United States Patent [19]

Strock

[11] Patent Number: 4,926,883
[45] Date of Patent: May 22, 1990

[54] PROTECTIVE BODY APPLIANCE

[76] Inventor: Alvin E. Strock, 647 Commonwealth Ave., Newton Center, Mass. 02159

[21] Appl. No.: 201,170

[22] Filed: Jun. 2, 1988

[51] Int. Cl.⁵ ............................................. A61F 13/00
[52] U.S. Cl. .................................... 128/888; 128/892
[58] Field of Search ...................... 128/888, 889, 95.1, 128/96.1, 100.1, 99.1, 846; 2/2, 22

[56] References Cited

U.S. PATENT DOCUMENTS

| | | | |
|---|---|---|---|
| 3,044,075 | 7/1962 | Rawlings | 2/22 |
| 3,526,221 | 9/1970 | Garber | 128/95.1 |
| 4,000,737 | 1/1977 | Horn | 128/154 |
| 4,134,399 | 1/1979 | Halderson | 128/132 R |
| 4,573,216 | 3/1986 | Wortberg | 128/846 |
| 4,633,863 | 1/1987 | Filips et al. | 128/846 |
| 4,641,641 | 2/1987 | Strock | 128/888 |

FOREIGN PATENT DOCUMENTS 269938 11/1950 Switzerland .

Primary Examiner—Robert A. Hafer
Assistant Examiner—Charles H. Sam
Attorney, Agent, or Firm—Nutter, McClennen & Fish

[57] ABSTRACT

A protective body appliance to prevent injury from external force to the underlying region of the wearer's body. The body appliance comprises a generally dome-shaped rigid shield secured to a flexible, compressible pad. The pad has an inner section that is adhered to the wearer's body, and an outer section to which the rigid shield is attached. The inner pad section has two lateral wings separated by a center region all of which form an exposed surface which is placed against the wearer's body. The inner pad section is mated to the outer pad section along the center region so that the wings are movable relative to the outer pad section. The wings permit the shield and outer pad section to shift or rock relative to the inner pad section in response to body movements and external forces, thus increasing the appliance's ability to remain adhered to the wearer over time.

14 Claims, 4 Drawing Sheets

PROTECTIVE BODY APPLIANCE

FIELD OF THE INVENTION

This invention relates generally to a user-worn appliance to protect against body injury, and more particularly to a user-worn appliance that can be worn for extended periods of time.

BACKGROUND OF THE INVENTION

An important consideration for many individuals is protecting localized, relatively vulnerable regions of their bodies from external forces likely to be experienced in their particular environments. These individuals include the elderly, others who suffer from degenerative tissue and bone structure changes, still others who are recovering from an illness or injury that has left a region of their bodies in a vulnerable state, and athletes who because of the activity in which they engage are vulnerable to injury. Often, persons with pre-existing medical conditions have one or more body regions that, if subjected to external force that would not affect a reasonably healthy person, could cause serious injury to an already vulnerable part of their bodies.

Illustrative of the types of persons often concerned with localized body region protection are those who, because of advanced age or past injury, are extremely prone to injury around the hip joint. The hip joint is a ball-and-socket joint formed by the reception of the ball-shaped head of the upper part of the femur into a cup-shaped cavity in the pelvis. Particularly vulnerable is the greater trochanter which protrudes outwardly from the femur just below the joint. This region is poorly protected by muscle and other soft body tissue of the type that surrounds the other regions of the hip. Hip joint injuries are especially common with the elderly and others who suffer from weakened bones, e.g., osteoporosis, those suffering from neurological disorders e.g., Alzheimer's disease, or those who require daily medication doses, which can cause them to be confused and make them susceptible to slips, tripping and falls.

Others frequently concerned about localized body region protection are those who, because of an illness or injury, are fitted with a partially or fully implanted medical device. For example, individuals with severe bone fractures often have the fractures secured by one or more implanted pins that, because of their orientation and design, extend close to or press against the inner surface of the skin. Pressure against this area even when sitting or sleeping can cause the skin to break down and ulceration to result. Bone securing pins of this type are commonly used in treating fractures of the hip joint.

Other partially or fully implanted medical devices requiring protection include hemodialysis connectors, medication diffusers, pacemakers, and the like. An external force directed to the region of the body in which such a medical device is fitted can disrupt the mounting of the device, causing it to malfunction or injure the skin or other body parts surrounding the device.

Certain individuals with the above described medical conditions also experience considerable discomfort and pain simply when reclining or sleeping in a position which causes pressure to be applied to the body region which is to be protected. This can be particularly troublesome for paraplegics or other individuals who, due to their age or the nature of their condition, are confined to beds for extended periods of time.

To date, various appliances have been suggested to protect localized body portions from external forces. One such appliance is disclosed in U.S. Pat. No. 4,641,461, to the inventor of the invention of this application, for a Protective Appliance For the Hip Joint Area. This appliance comprises a flexible pad adhesively secured to the wearer and a rigid shield removably secured to the pad. The shield is configured to absorb and disperse external forces to which it is exposed so as to prevent the underlying vulnerable body region from suffering their effects. This appliance is typically worn on the skin over the region of the greater trochanter to protect against hip injury.

One major limitation of many prior adhesively secured protective appliances is that they tend to "wear" off the user with time. Simple body movements cause sections of the adhesively secured pad to be pulled away from the skin. Though the sections may re-adhere to the body in later movements, the bonding strength of the adhesive is substantially weakened. Consequently, over time, the adhesive securing the appliance becomes so weak it can no longer hold the appliance to the body. As a result, the appliance falls off the user and usually has to be replaced. Pad separations of this type occur over time even with bedridden users whose body movements while turning in bed are slight.

The short lifetimes of protective appliances resulting from repetitive pad separations of this type create various problems for their users. If the appliance user is a person suffering from a medical condition requiring long-term protection of a body region, he or she may be forced to spend considerable, possibly burdensome, sums of money frequently replacing the appliance. Furthermore, when the user is incapable of personally applying the appliance to his or her own skin, there are additional expenses associated with caregivers being required continually to check the user to verify that the appliance is in place, and when it is not, to replace it with a new one. This latter situation and associated expense arise frequently with comatose and geriatric persons whose medical condition necessitates long-term wearing of the appliances.

Moreover, prior protective appliances of this type are not well suited for active individuals whose need is limited to protection for one small region of their bodies, such as the hip joint area, that normally undergoes frequent movement such as during walking and the like. Individuals wearing such appliances may find that their normal day-to-day body movements cause the appliances to separate from their bodies in short order. If such individuals do not carry replacements with them during the desired activity, they are often forced to forego protection altogether.

SUMMARY OF THE INVENTION

This invention provides a novel protective body appliance that covers a localized region of the body, such as the hip joint, to guard against injury due to external forces, and that can be worn for extended periods of time without replacement.

The protective body appliance of this invention includes a relatively rigid shield attached to a relatively flexible, relatively compressible pad. The rigid shield, which in the preferred embodiment is dome-shaped, protects the underlying region of the wearer's body. The pad may include a first section to which the rigid shield is attached, and a second section for securing the protective body appliance to the wearer. The second section of the pad includes two lateral wings separated by a center portion that is attached to the first section of the pad. An appropriate adhesive is applied to the underlying or exposed surface of the second pad section for securing the appliance to the skin of the wearer.

The protective body appliance is used by securing it to a selected region of the wearer's body especially prone to injury due to external forces. The adhesive on the second section of the pad has sufficient bonding properties to secure the protective body appliance to the user. The shield absorbs and deflects or disperses external forces to which it is exposed so that the underlying vulnerable body region is shielded from the same and their potentially damaging effects. The pad also cushions the effect of these forces on the body.

The provision of the lateral wings on the second section of the pad allows for a limited degree of rocking movement between the shield and the pad. In other words, when the second pad section is secured to the skin of the wearer, the first pad section, to which the rigid shield is attached, can move or rock relative to the second pad section. Thus, when the protective body appliance experiences movements that might otherwise break the adhesive bond between the skin of the wearer and the pad, the rigid shield and first pad section move in a rocking motion while the second pad section remains attached to the wearer. As a result, the likelihood that the adhesive bond securing the appliance to the wearer will break is substantially reduced. Consequently, the adhesive bond is able to hold the protective body appliance to the wearer for extended periods of time so that the appliance has an extended usable lifetime.

Different embodiments of the protective body appliance may be provided that offer the above noted advantage of longer useful lifetimes, as well as others. The rigid shield may be removably attached to the pad, for example, by allowing the shield ends to be received in pockets in the first section of the pad, or to be fastened thereto with snap rivets, tabs, or Velcro hook and loop strips. This allows the rigid shield to be removed from the pad either for treatment of the wearer while the pad remains attached to the skin, or when the pad is to be replaced with a new one. One or more vent openings may be formed in the second pad section to expose the underlying skin to air. The air exposure allows the underlying skin to breath and perspiration to evaporate. In appropriate cases, the openings may also be used to selectively reduce the adhesive-skin contact area so as to reduce the discomfort associated with removing the pad. Additionally, medication may be applied to the pad adhesive so that when the protective body appliance is secured to the wearer, the medication will diffuse into the skin of the wearer. Numerous other advantages may be realized with the below-described embodiments of the invention.

DETAILED DESCRIPTION OF THE PREFERRED EMBODIMENT

Figure 1:
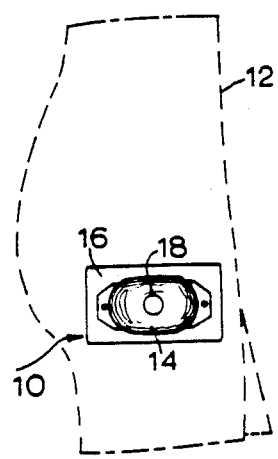
FIG. 1 illustrates a protective body appliance embodied in accordance with this invention secured to the hip joint area of a human subject depicted in broken lines.

FIG. 1 depicts a protective body appliance 10 embodied in accordance with the present invention secured over the hip joint region of a human wearer 12. The protective body appliance 10 comprises a relatively rigid shield 14 attached to a relatively flexible, relatively compressible pad 16. In the illustrated use of the protective body appliance 10, it is positioned to protect the greater trochanter of the wearer's hip joint region. The protective body appliance 10 is secured over the greater trochanter region in a generally horizontal orientation by visual and tactile location of a depression in the hip created by muscle and bone structure in this region of the body. An opening 18 formed in the pad 16 aids in the proper location of the appliance on the body, and in providing ventilation for the underlying skin.

Figure 2:
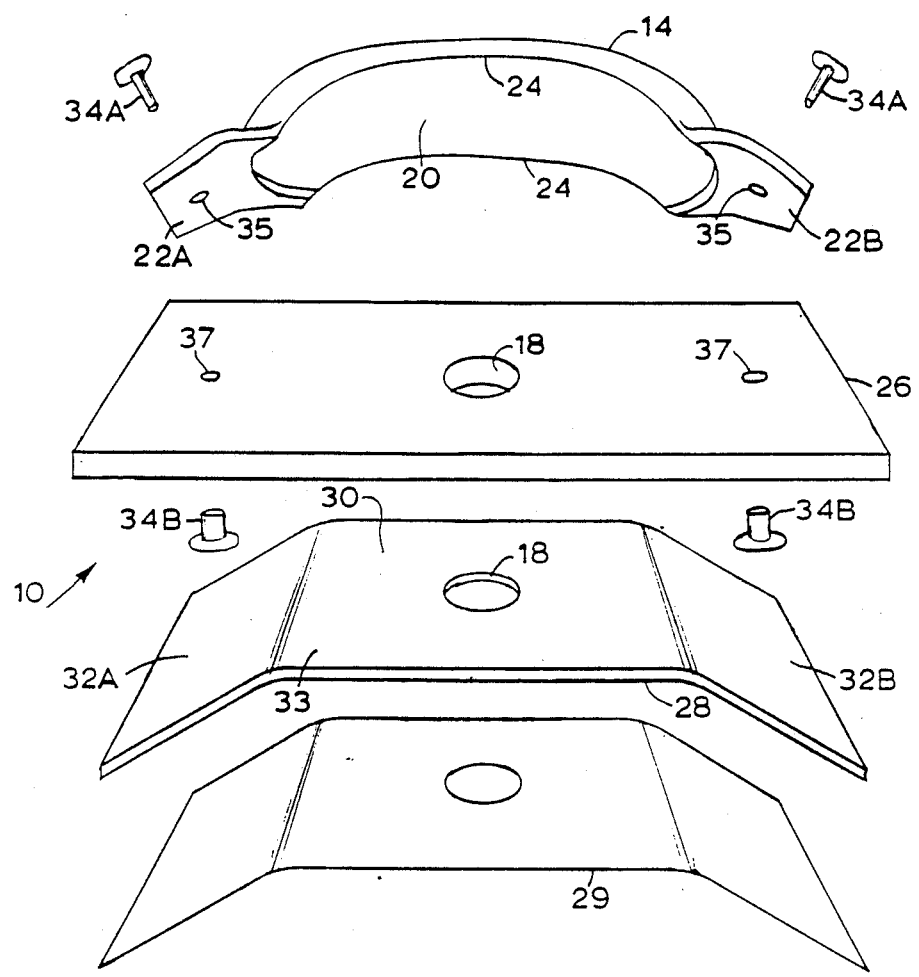
FIG. 2 is an exploded view of the protective body appliance of the invention.

Referring to the exploded view of FIG. 2 of the drawing, the protective body appliance 10 is shown in greater detail. The rigid shield 14 is formed from a single piece of impact resistant material that is illustratively transparent, such as the clear polycarbonate plastic marketed under the trademark LEXAN, or other suitable material. The transparency of the shield 14 material assists in locating it on the body and in enabling visual inspection of body region which it overlies. The rigid shield 14 has a main body portion 20, which is generally dome-shaped and has an approximately elliptical plan view cross-sectional area. Integral with the main body portion 20 are two flanges 22A and 22B, one at each end of the main body portion 20. The flanges 22A and 22B have sufficient surface area so that they lessen the effect of any force that is applied to the rigid shield 14. In the illustrated embodiment of the invention, the main body portion 20 of the shield 14 subtends an area of approximately 7.5 × 13 centimeters, and has a height above the horizontal of approximately 1.3 centimeters. The flanges 22A and 22B each subtend an area of approximately 1.8 by 4 centimeters. The shield 14 is approximately 3 millimeters thick.

The main body 20 of the shield 14 includes a pair of arcuate edges 24 that extend along its sides from flange 22A to flange 22B. The edges 24 are curved upwardly from the plane of the flanges 22A and 22B so that when the shield 14 is attached to the pad 16, as described below, the edges 24 are spaced above the pad 16. This prevents the edges 24 from pressing into the pad and against the wearer when the appliance is pressed against the body due to body movements or the impact of external forces. The flanges 22A and 22B are also curved slightly to approximate the curvature of the body region to which the protective body appliance 10 is to be secured.

The pad 16 is preferably made of a closed cell polyethylene foam which is inert and gentle to the skin, and may have a density of approximately 6 pounds per cubic foot. The pad 16 comprises a first section 26 to which the rigid shield 14 is attached, and a second section 28 that is adapted to be adhesively secured to the wearer 12. The second pad section 28 includes a center portion 30 that is mated to a corresponding center region of the first pad section 26. Integral with the center portion 30 are two lateral wings 32A and 32B, one on each side of the center portion 30, and located approximately underneath the shield flanges 22A and 22B. The underside of the center section 30 and wings 32A and 32B together define a single, substantially continuous surface area 33 for contacting the skin. The pad opening 18, which is formed through both the first pad section 26 and second pad section 28, is approximately 2 centimeters in diameter.

The pad 16 is dimensioned so that the first section 26 subtends an area slightly greater than that of the shield 14. In this embodiment of the invention, the first pad section 26 has dimensions approximately $8 \times 13 \times 0.5$ centimeters, and the second pad section 28 has dimensions of approximately $8 \times 11 \times 0.3$ centimeters.

A suitable hypo-allergenic medical adhesive is applied to the exposed contact surface 33 of the second pad section 28 for purposes of securing the protective body appliance 10 to the skin of the wearer 12. A removable covering 29 covers and protects the adhesive prior to the protective body appliance 10 being secured in place.

In this illustrated embodiment of the protective body appliance 10, snap rivets are used to removably attach the shield 14 to the pad 16. The snap rivets comprise a male part 34A and a female part 34B which can be snapped and unsnapped relative to one another as desired. The rivets extend through openings 35 formed in the shield flanges 22A and 22B and through openings 37 formed in the first section 26 of the pad 16. The rivets 34 allow the selective removal of the shield 14 from the pad 16, and also allow the shield 14 to be removed from a soiled, unsanitary or poorly adhered pad 16 and placed on new one. In this respect, the protective appliance 10 may advantageously be packaged and sold as a kit which includes two shields 14 (e.g., one for each side of the body) and several pads 16 which can be replaced whenever the need arises. The rivets 34, the flange openings 35, and the pad openings 37 are preferably dimensioned to allow a limited degree of movement between the shield 14 and the pad 16 in response to body movements.

The appliance 10 is used by removing the protective covering 29 from the adhesive on the second pad section 28 and pressing the appliance 10 against the appropriate body region of the wearer 12 to be protected. As already noted, the transparency of the shield 14, the pad opening 18 and the lateral spacing between the shield 14 and the pad 16 make it possible to insure by visual and/or tactile examination that the appliance 10 is properly secured over the desired body region. The flexibility of the second pad section 28 allows it to bend into conformity with the body region to which it is adhered, providing contact over substantially the entire area of the adhesive.

Once the body appliance 10 is adhered to the wearer 12, the rigid shield 14 absorbs and deflects or disperses external forces that would otherwise impact the covered body region. Forces that are transferred through the shield 14 to the pad 16 are dispersed through a wide body area by the flanges 22A and 22B. Forces transferred to the pad 16 are also attenuated due to its compressibility.

The lateral wings 32A and 32B on second pad section 28 provide the first pad section 26 and shield 14 with freedom of rocking movement relative to the second pad section 28. This allows the shield 14-first section 26 sub-assembly to shift positions in response to body movements and external forces without causing the second pad section 28 to be torn from the wearer 12.

Accordingly, when the wearer 12 is sleeping or otherwise exposing the appliance 10 to forces that tend to tear it from the wearer's body, the shield 14 and first pad section 26 may rock or shift position while the second pad section 26 remains secured to the wearer 12. The appliance 10 will thus stay firmly affixed to the wearer for an extended period of time, in some instances a month or more. This is a particularly important consideration in a custodial care environments where the wearer 12 requires substantially continuous protection and is often in a recumbent position and in contact with chairs, mattresses and the like that cause the appliance to shift and thus fall off the wearer.

There are significant cost savings associated with this protective body appliance 10. Since the lateral wings 32A and 32B of second pad section 28 function to hold the appliance 10 to the wearer 12 for extended periods of time, the appliance 10 does not have to be replaced frequently. Also, as noted above, the shield 14 can readily be detached and reattached to a new pad 16 as the need arises. Accordingly, the cost of providing protective body appliances 10 for a wearer 12 requiring protection for long periods of time is reduced. Further cost advantages are achieved in custodial care environments because caregivers need not frequently replace protective body appliances 10 that have separated from the wearer 12.

Figure 3:
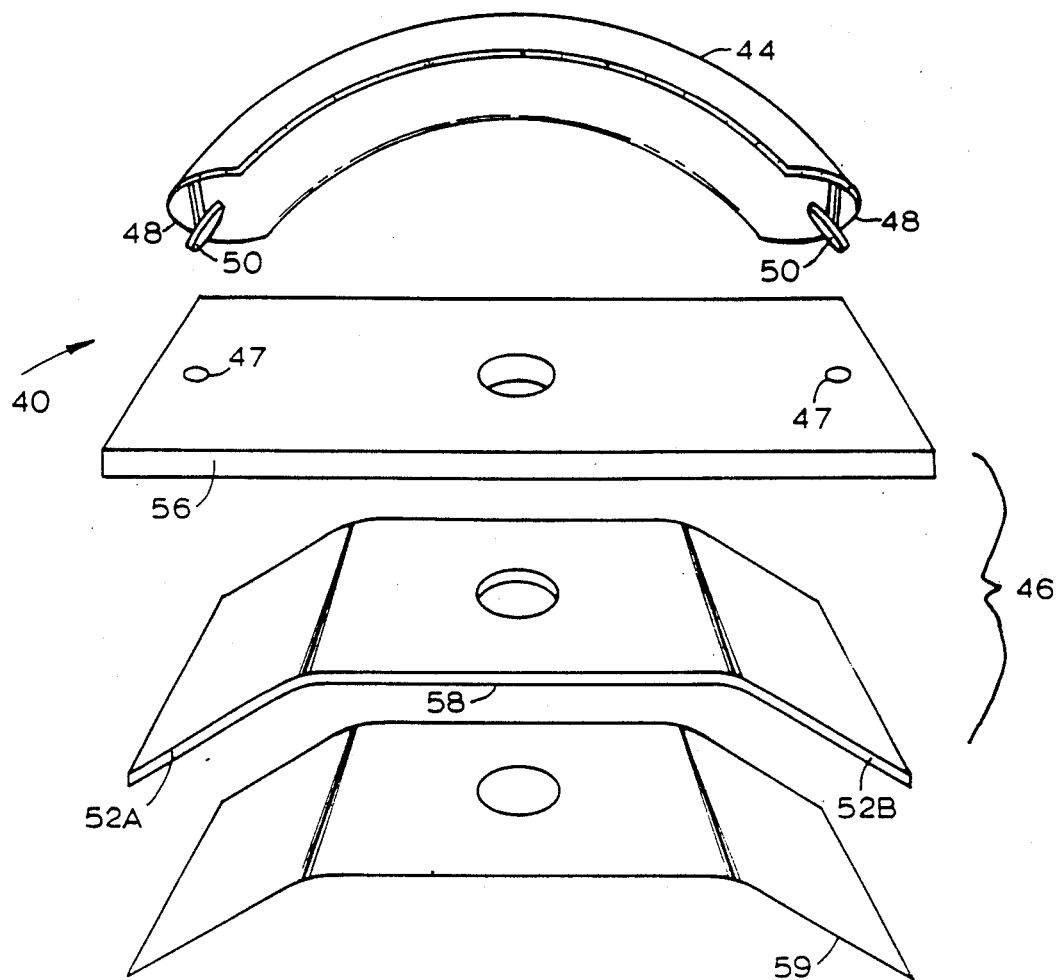
FIG. 3 is an exploded view of a second embodiment of a protective body appliance constructed in accordance with this invention.

An alternative embodiment of the protective body appliance of the present invention, referred to generally by reference number 40, is depicted by FIG. 3. The protective body appliance 40 includes a relatively rigid shield 44 releasable secured to a relatively flexible, relatively compressible pad 46 that is substantially identical to the flexible pad 16 of the first embodiment of this invention.

The rigid shield 42 has a generally curved longitudinal profile, which is convex in shape when viewed relative to the flexible pad 46. It defines end edges 48 that are relatively flat and substantially coplanar so as to provide a relatively unobtrusive edge for contacting the pad 46. Indeed, the shield 42 in this configuration and construction may have a limited degree of flexibility to it so that when shield 42 is urged against the pad 42 by external forces, it will tend to flatten slightly rather than having its end edges 48 become embedded in the pad 42.

The rigid shield 44 is removably secured to the pad 46 by downwardly extending tabs 50 integral with the shield near its end edges 48. The tabs 50 are fitted into openings 47 formed in outer pad section 56. The tabs 50 and openings 47 are preferably dimensioned relative to each other so as to allow for limited movement of the shield 44 relative to the pad 46 and for limited flattening of the shield 44 that may occur when it is subjected to a large external force.

As in the case of the pad 16 of protective body appliance 10 of FIG. 2, the pad 46 of the appliance 40 includes a first pad section 58 that has lateral wings 52A and 52B which are free to move relative to a second pad section 56. Again, this permits the shield 44 and second pad section 56 to shift or rock relative to the first pad section 58 during body movements and in response to external forces, thus assuring that the adhesive undersurface of the second pad section 58 remains affixed to the wearer's skin. Again, a protective covering 59 is provided for the adhesive.

The protective body appliance 40 is used in a manner similar to the protective body appliance 10 of the first embodiment of the invention. The shield 44 absorbs and deflects or disperses external forces applied thereto so that they are distributed away from the protected body region. The arrangement of the end edges 48 allows the shield 44 to flatten somewhat against the pad 46 when it is exposed to a large external force and to distribute such force throughout a relatively large area of the compressible pad 46. The appliance 40 thus effectively blunts any forces that would otherwise strike the underlying vulnerable body region so that the covered body region is protected from injury.

The rigid shield 44 of the protective body appliance 40 can be economically manufactured by conventional molding techniques. A further cost saving is achieved with the appliance 40 by virtue of the tabs 50 which eliminate the need to provide separate, more costly securing means such as the snap rivets 34 of the first embodiment.

Figure 4:
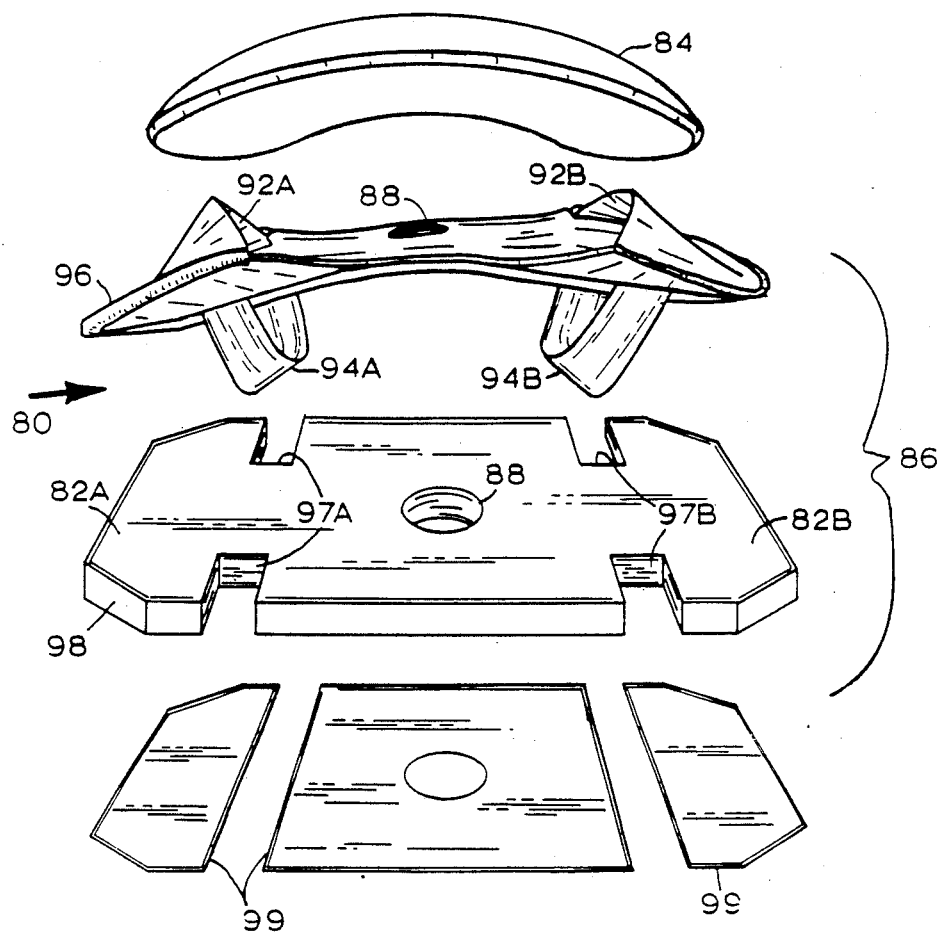
FIG. 4 is an exploded view of a third embodiment of a protective body appliance constructed in accordance with this invention.

A third embodiment of the invention is illustrated in FIG. 4 of the drawing. Protective body appliance 80 includes a relatively rigid, generally dome-shaped shield 84 that is removably secured to a multi-section, relatively flexible, relatively compressible pad 86. Unlike the prior shields 14 and 44, the shield 84 has neither end flanges nor tabs. The pad 86 includes a first section 96 and a second section 98. The inner pad section 96 is provided with a pair of counter-opposed pockets 92A and 92B that are adapted to receive and hold the counter-opposed ends of the shield 84. Thus, the shield 84 may be secured relative to the pad 86 by inserting its ends in the opposed pockets 92A and 92B, and removed from the same when the need arises. Preferably, the fit of the shield ends in the pockets 92A and 92B is such that a limited degree of movement is permitted between the shield 84 and first pad section 96 in response to body movements. Beneath each pocket 92A and 92B, the first pad section includes a strap 94A and 94B, respectively, the function of which is described immediately below.

The second pad section 98 comprises a relatively thick, relatively compressible material whose subtended area is somewhat greater than the subtended area of the first pad section 96. The second pad section 98 includes two pairs of opposed notches 97A and 97B which are spaced apart from one another by the same spacing that exists between the straps 94A and 94B on the first pad section 96. As should be apparent, the notches 97A and 97B are adapted for engagement by the straps 94A and 94B to thereby removably secure the second pad section 98 to the outer pad section 96. The engagement of the straps 94A and 94B in the notches 97A and 97B prevents the second pad section 98 from sliding or shifting laterally relative to the first pad section 96. For this purpose, the straps 94A and 94B may be formed of an elastic material that can be stretched to permit easy insertion of the second pad section 98 and that elastically contracts when released to hold the inner pad section 98 firmly in place.

A suitable adhesive is provided on the undersurface of the second pad section 98 for adhering the appliance 80 to the skin of the wearer. A removable covering 99 protects the adhesive until the appliance 80 is ready for use. Also as in the previous embodiments, openings 88 extend through the first pad section 96 and second pad section 98 to assist in locating the appliance 80 on the wearer and in providing proper ventilation.

The protective body appliance 80 of FIG. 4 has the same desirable features and advantages as the previously described embodiments, as well as others which are unique to it. As with the previous embodiments, the strap-notch attachment arrangement in appliance 80 has the effect of providing a pair of lateral wings 82A and 82B which are free to flex and move relative to the first pad section 96. The shield 84 and first pad section 96 are thus free to shift and rock relative to the second pad section 98 in response to body movements and external forces, while the second pad section 98 remains securely adherely to the skin of the wearer. Thus, the useful lifetime of the adhesive is extended.

The shield 84 of the appliance, 80 is particularly inexpensive to fabricate by conventional molding techniques due to the absence of any flanges, holes or tabs. Additionally, because in this embodiment the second pad section 98 is removable from the first pad section 96, the shield 84 and first pad section 96 may be treated as the relatively permanent portions of the appliance 80, while the relatively inexpensive and simple second pad section 98 may be treated as the relatively disposable portion of the appliance 80, subject to more frequent replacement.

The described embodiments of the invention are preferably configured and dimensioned to cover and protect the wearer's hip joint. It is readily apparent, however, that the invention can be used to protect other body regions. For example, an individual with an implanted medication-release membrane can wear a protective body appliance of this invention to guard the membrane from physical blows that might otherwise dislodge it, or cause an excess release of medication. The protective body appliance may additionally be provided with a so-called "painless" medical adhesive, for example, of the type marketed under the tradename HYDROGEL. Such adhesives generally have good adhesion properties, but are more readily peeled from the skin when time comes for the appliance to be removed from the wearer. Such adhesives are particularly useful for athletes and the like who apply the appliance during a given athletic activity and remove it after completion of the same.

The protective body appliances of the invention also have applications for protecting surgical wounds. The appliances would, of course, protect the wound stitching and wound area. A further advantage of the appliances in this respect is that post-operative care of the wound is simplified since access to the wound area is gained by simply removing the rigid shield. For this purpose, the pad of the appliance may be provided with a relatively large opening that permits visual inspection of a large area under the shield. After the wound is inspected, the rigid shield can be reattached. This eliminates the need to remove a bandage and rebandage the wound each time access to it is required.

Still other changes and enhancements to the protective body appliances of this invention are possible. For example, in the first two described embodiments of the invention, the first section and inner section of the pad are formed from two sections of foam material that are mated, e.g., glued, together. In other versions of the protective body appliance, they may be formed from a single piece of flexible, compressible material. That single piece pad may be partially sliced through its ends to form the lateral wings. Alternatively, means for holding the shield to the pad may be formed integrally with a single piece pad in such a way as to provide the desired lateral wings. In this respect, straps like the straps 94A and 94B may be provided on the exposed (When the pad is applied to the body) surface of the pad to hold the shield in place. Furthermore, the protective body appliances of each embodiment can be configured and dimensioned, including with proper curvature, so that they can be fitted to and protect other body regions besides the hip, and can also be dimensioned to fit children, infants and the like. An example of this is protecting growth centers of young adolescents during sport activities.

The protective covering over the adhesive on the undersurface of the second pad section may also be slit or sectioned. This allows only sections of the covering to be removed exposing less than all of the adhesive area in those cases where weaken adhesion is desired. Medication may also be mixed with the adhesive. When the protective body appliance is secured against the wearer, the medication would diffuse into the wearer's body through the skin so that the wearer would receive its beneficial effects.

Thus, the foregoing detailed description has been limited to the specific embodiments of the invention. It will be apparent, however, that variations and modifications can be made to the described embodiments with the attainment of some or all of the advantages of the invention. Therefore, it is the object of the appended claims to cover all such variations and modifications as come within the true spirit and scope of the invention.

What is claimed as new and desired to be secured by Letters Patent of the United States is:

I claim:

1. A protective body appliance to be secured to a wearer, comprising:
    a pad formed from a relatively flexible, relatively compressible material having a first section and a second section, said second section having a surface for positioning against the wearer, and including a pair of opposed end wing portions that are flexible relative to said first pad section when said second section is adhered to the wearer;
    means for adhering said second pad section surface to the wearer; and
    a relatively rigid shield having opposed ends secured to said first pad section so that a central portion of the shield is raised above said pad and so that said shield is permitted a limited degree of rocking movement relative to wing portions of said second pad section when said second pad section surface is adhered to the wearer, said shield being adapted to absorb and disperse forces applied thereto, transferring such forces to areas spaced away from said central portion of said shield.

2. A protective body appliance as described in claim 1 in which said shield is generally dome shaped.

3. A protective body appliance described in claim 1 wherein said means for adhering said second pad section to the wearer comprises an adhesive substance applied to said second pad section surface.

4. A protective body appliance as set forth in claim 1 wherein said shield is removably secured to said first pad section.

5. A protective body appliance as set forth in claim 1 wherein an opening is provided centrally through the pad.

6. A protective body appliance as set forth in claim 1 wherein said second pad section and said first pad section comprise separate pieces secured together at a center region of said second pad section so as to define said wing portions.

7. A protective body appliance as set forth in claim 1 wherein said second pad section and said first pad section are formed integrally from a single piece of relatively flexible, relatively compressible material.

8. A protective body appliance as set forth in claim 1 wherein said shield includes opposed, outwardly extending flanges substantially in face-to-face contact with said first pad section.

9. A protective body appliance as set forth in claim 8 wherein said shield is removably secured to said first pad section by fastening means which engage said flanges and ends of said first pad section.

10. A protective body appliance as set forth in claim 4 wherein said shield includes integral tabs at its opposed ends for removably engaging in corresponding holes provided in said first pad section thereby permitting said shield to be removably secured to said first pad section.

11. A protective body appliance as set forth in claim 4 wherein said first pad section includes a pair of opposed pockets for removably receiving opposed ends of said shield thereby permitting said shield to be removably secured to said first pad section.

12. A protective body appliance as set forth in claim 6 wherein said first pad section includes a pair of spaced apart straps for removably engaging in corresponding notches provided in the center region of said second pad section thereby permitting said first pad section to be removably secured to said second pad section.

13. A protective body appliance as set forth in claim 12 wherein said straps are formed of an elastic material.

14. A protective body appliance as set forth in claim 3 further including a removable covering for the adhesive.

* * * * *